United States Patent [19]

Carnahan

[11] 4,277,628
[45] Jul. 7, 1981

[54] PHENOL RECOVERY FROM BISPHENOL-A WASTE STREAMS

[75] Inventor: James C. Carnahan, Schenectady, N.Y.

[73] Assignee: General Electric Company, Schenectady, N.Y.

[21] Appl. No.: 151,664

[22] Filed: May 20, 1980

[51] Int. Cl.$^3$ ............................ C07C 37/68; C07C 37/74
[52] U.S. Cl. ......................................... 568/749; 568/724; 568/753
[58] Field of Search ........................ 568/749, 806, 724

[56] References Cited

U.S. PATENT DOCUMENTS 3,466,337  9/1969  Smith et al. ........................ 568/806

FOREIGN PATENT DOCUMENTS 1493508  3/1970  Fed. Rep. of Germany ........... 568/806
880895  10/1961  United Kingdom ...................... 568/806
583996  12/1977  U.S.S.R. ................................... 568/749

Primary Examiner—Werren B. Lone
Attorney, Agent, or Firm—Joseph T. Cohen; James C. Davis, Jr.

[57] ABSTRACT

Bisphenol-A waste stream derived from the reaction of phenol and acetone in the presence of an acidic condensing agent can be treated with aluminum isopropoxide to obtain good yields of phenol present in the effluent stream either in isolated form or as part of the compounds present in the waste stream.

4 Claims, No Drawings

PHENOL RECOVERY FROM BISPHENOL-A WASTE STREAMS

This invention is concerned with a process for obtaining phenol from the residue derived during the manufacture of bisphenol-A [2,2-bis(4-hydroxyphenyl)propane], hereinafter also identified as "BPA". More particularly, the invention is directed to a method for recovering phenol from the residual tar (or waste stream) resulting from the reaction of phenol and acetone in the presence of an acidic condensation catalyst from which most of the bisphenol-A has been removed, by treating the said tar with an effective amount of aluminum isopropoxide having the formula:

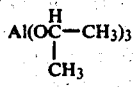

I.

and thereafter isolating the phenol thereby present in said waste stream or liberated by such treatment.

Bisphenol-A is commercially prepared by reacting phenol and acetone in the presence of an acidic material such as sulfuric acid, hydrochloric acid, cation exchange resins, etc. As a result of carrying out this reaction, the bisphenol-A produced is accompanied by undesirable impurities such as the 2-(4-hydroxyphenyl)-2-(2-hydroxyphenyl) propane (hereinafter identified as "o,p-isomer") having the formula:

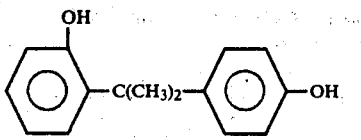

II.

as well as other impurities including the reactant phenol itself used in making the bisphenol-A, a trishydroxyphenyl compound of the formula

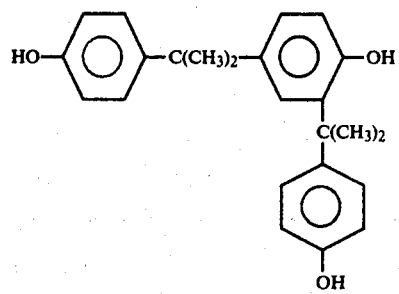

III.

(hereinafter identified as "BPX-1"), small amounts of other impurities such as the two compounds having the formulas

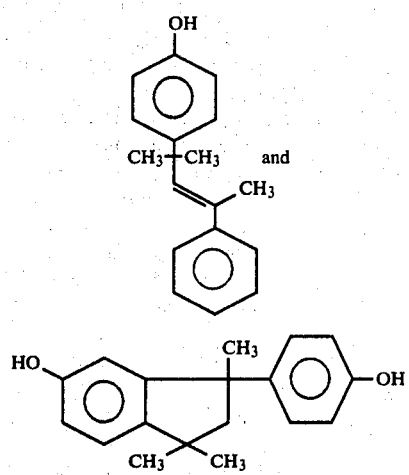

IV.

(hereinafter identified as "LD/CD", Chroman I of the formula

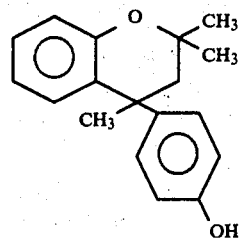

V.

and Chroman II of the formula

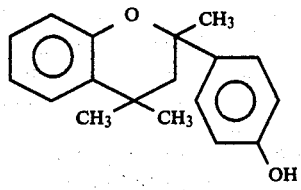

VI.

The bisphenol-A produced by the above method has in the main been effectively removed from the tarry residue by a number of procedures, including distillation, crystallization, solvent extraction, spray drying, etc. There still remains the need to efficiently treat the tars and residues resulting from the initial reaction of the phenol and acetone and recover all useful products possible in order to enhance the bisphenol-A process. Included in the tars derived from the bisphenol-A reaction are certain amounts of bisphenol-A itself which is trapped therein, as well as the aforementioned free phenol. If a method could be obtained for economically and efficiently treating the residue of the bisphenol-A reaction (hereinafter also referred to as "residue"), it has been calculated that millions of pounds of phenol could be recovered derived from compounds present in the residue which when cracked will provide phenol, particularly from the compounds II to VI mentioned above.

Heretofore no useful process to my knowledge has been found for cracking the tars or treating the tars in such a manner as to make it worthwhile to expend the extra effort and energy to recover phenol from the residue. As a result, the usual solution to disposal of the residue involves treating the residue as a source of energy by burning it. Unexpectedly, I have discovered that I can treat the residue with relatively small amounts of aluminum isopropoxide at relatively modest temperatures and at atmospheric pressure, for instance, at temperatures ranging from about 150° to 300° C. whereby treated residue can then be distilled to remove substantially all of the phenol liberated from compounds in which the phenol ion was part of a compound present in the tarry residue.

The use of the aluminum isopropoxide has several advantages. In the first place, the aluminum isopropoxide is readily available on the open market and is relatively cheap. Secondly, being readily available, it is not necessary to make the aluminum isopropoxide in a plant where bisphenol-A is being made with the attendant hazard of hydrogen formation when one attempts to make, for instance, either aluminum isopropoxide separately or aluminum phenoxide which has in the past been used for dealkylation of compounds such as 4-t-butylphenol tetramethylbutylphenol, etc. To the best of my knowledge, no one has ever tried to treat the tars or residues derived from the bisphenol-A production process with any aluminum compound and certainly not with aluminum isopropoxide.

I am aware that British Pat. No. 940,378 suggests the use of either aluminum or aluminum phenoxide as a means for dealkylating alkylated phenols some of which have been mentioned above. However, if one uses aluminum for treatment of the residue obtained from the bisphenol-A production, there is again the danger of hydrogen being formed which introduces a hazard into the procedures for isolating phenol. In addition, aluminum phenoxide is so expensive and substantially unavailable, that its use for treatment of the residue is not attractive. Moreover, although aluminum phenoxide has been used as described in the aforesaid British patent, for dealkylating paraalkylated phenols, there is not the slightest suggestion in this patent of the use of any aluminum compound, and certainly not aluminum isopropoxide, for treating the residue derived during the bisphenol-A production to obtain and isolate phenol derived from complex compounds in the residue.

The residue often contains as much as 50 weight percent unrecovered bisphenol-A together with small amounts of the o,p-isomer and other phenol-based compounds. The residue is a solid material which at room temperature softens with increased heating and becomes fluid at around 100° C.

The amount of aluminum isopropoxide which can be employed can be varied widely and generally the residue is not sensitive to the amount of aluminum isopropoxide used. Advantageously, I can employ on a weight basis, from 0.005 to about 5%, by weight, and preferably from 0.05 to 1%, by weight, of aluminum isopropoxide, based on the weight of the residue. Generally, the residue is not so different that any material change in the concentration of the aluminum isopropoxide will cause any undesirable variation in the amount of phenol which may be obtained or liberated.

The temperature at which the reaction is carried out can be varied widely but is usually that which is high enough to effect the desired liberation of the derived phenol. The fact that some bisphenol-A is present also will result in the latter releasing phenol as a result of practicing the invention. Generally temperatures on the order of about 150° to about 300° C. or even higher (but below the decomposition point of any of the compounds in the residue) can be employed without departing from the scope of the invention. The temperature used will depend on the rate of reaction desired, the concentration of phenol and other byproducts in the residue on which the aluminum isopropoxide is intended to act, the amount of aluminum isopropoxide used, etc. Although the reaction is more conveniently carried out at atmospheric pressure, superatmospheric and subatmospheric pressures are not precluded.

In order that those skilled in the art may better understand how the present invention may be practiced, the following examples are given by way of illustration and not by way of limitation. All parts are by weight unless otherwise indicated.

EXAMPLE 1

In this example, a residue obtained from the reaction of phenol and acetone to make bisphenol-A using HCl as a condensation catalyst was employed for the purpose of treatment with aluminum isopropoxide. The residue used in this example contained about 32% residual bisphenol-A with varying amounts of the o,p-isomer and other impurities of formulas III to VI together with a variety of related phenol-based structures. The treatment with the aluminum isopropoxide was carried out in a three-neck round bottom flask fitted with a thermometer and Claissen type still head. A Teflon coated magnetic stirring bar provided agitation, and the reaction was heated with an electric heating mantle. Mixtures of the residue and specified amounts of the aluminum isopropoxide were heated and the products collected.

The amount of aluminum isopropoxide used was 0.2 weight percent based on the weight of the residue, and the time of heating varied from 0–60 minutes. The following Table I shows the effect of heating the residue (300 grams) both with and without the aluminum isopropoxide, and illustrates clearly the accelerated rate at which the phenol is removed from the residue using the aluminum isopropoxide in contrast to the test where no catalyst was employed.

TABLE I

| | Elapsed Time Minutes | Pot Temp. °C. | Cumulative Phenol Yield (Grams) |
| --- | --- | --- | --- |
| Test 1 | | | |
| 0.6 gram Aluminum Isopropoxide | 0 | 180 | — |
| | 12 | 260 | 3.68 |
| | 27 | 263 | 86.28 |
| | 45 | 295 | 138.78 |
| | 55 | 300 | 145.1 |
| Test 2 | | | |
| No Catalyst | 0 | 180 | — |
| | 16 | 285 | 4.81 |
| | 30 | 275 | 34.65 |
| | 45 | 310 | 68.12 |
| | 60 | 300 | 71.00 |

The total distillate for Test 1 was 153.6 grams of which 94.4% was recovered phenol for a net yield of 48.3% phenol based on the residue. When no catalyst was used, 84.7 grams total distillate was obtained for a net yield of 23.8% phenol, based on the weight of the residue initially employed.

It will of course be apparent to those skilled in the art that in addition to the conditions, proportions of ingredients, and catalyst concentration used above, other conditions, proportions of ingredients, and concentrations of aluminum isopropoxide may be employed within the scope of the claimed invention.

What I claim as new and desire to secure by Letters Patent of the United States is:

1. The process for producing liberated phenol by cracking a tarry residue derived from the acid reaction of phenol and acetone thereby to make bisphenol-A, which process comprises heating the said residue with aluminum isopropoxide at a temperature in excess of 150° C., but below the decomposition point of any of the compounds in the residue in an amount of aluminum isopropoxide and for a time sufficient to cause distillation of liberated phenol from the residue, and thereafter collecting the distilled phenol.

2. The process in claim 1 wherein the temperature of reaction ranges from 150°–300° C.

3. The process in claim 1 wherein the amount of aluminum isopropoxide ranges from about 0.005 to 5%, by weight, based on the weight of the residue.

4. The process in claim 1 wherein the temperature is within the range of from about 150°–300° C. and the aluminum isopropoxide is in an amount equal to from 0.05 to 1%, by weight, based on the weight of the residue.

* * * * *